US007521566B2

(12) United States Patent  (10) Patent No.: US 7,521,566 B2
Datta et al.  (45) Date of Patent: Apr. 21, 2009

(54) PROCESS FOR PREPARATION OF PERINDOPRIL AND SALTS THEREOF

(75) Inventors: Debashish Datta, Pune (IN); Girij Pal Singh, Pune (IN); Himanshu Madhav Godbole, Pune (IN); Rajinder Singh Siyan, Pune (IN)

(73) Assignee: Les Laboratoires Servier, Courbevoie Cedex (FR)

( * ) Notice: Subject to any disclaimer, the term of this patent is extended or adjusted under 35 U.S.C. 154(b) by 274 days.

(21) Appl. No.: 10/547,243
(22) PCT Filed: Feb. 28, 2003
(86) PCT No.: PCT/IN03/00042

§ 371 (c)(1),
(2), (4) Date: Jun. 21, 2006

(87) PCT Pub. No.: WO2004/075889
PCT Pub. Date: Sep. 10, 2004

(65) Prior Publication Data
US 2006/0276659 A1   Dec. 7, 2006

(51) Int. Cl.
*C07D 209/42* (2006.01)
(52) U.S. Cl. ..................................... 548/492
(58) Field of Classification Search .................. 548/492
See application file for complete search history.

(56) References Cited
U.S. PATENT DOCUMENTS

| 4,508,729 A | 4/1985 | Vincent et al. |
| 4,902,817 A | 2/1990 | Vincent et al. |
| 4,914,214 A | 4/1990 | Vincent et al. |

FOREIGN PATENT DOCUMENTS

DE   197 21 290   12/1997

(Continued)

OTHER PUBLICATIONS

Wikipedia, the free encyclopedia.*

(Continued)

*Primary Examiner*—Rei-tsang Shiao
(74) *Attorney, Agent, or Firm*—Hueschen and Sage

(57) ABSTRACT

A process for preparation of perindopril of formula (II) and salts thereof

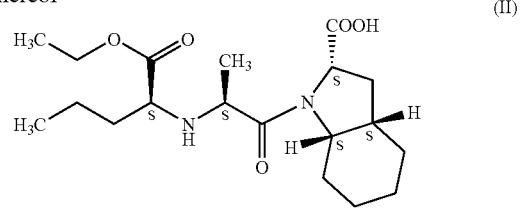

which is simple, safe, convenient and cost-effective.

The process involves reaction of compound of formula (I),

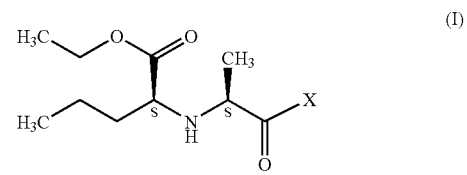

wherein X is chlorine or bromine
with compound of formula (VII)

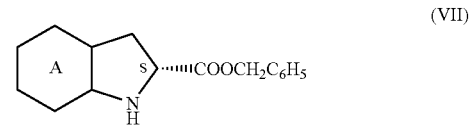

wherein A signifies that the six-membered ring of the bicyclic system is either saturated or unsaturated to give compound of formula (VIII),

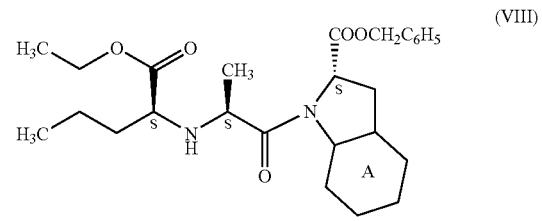

wherein A is as defined above,
followed by catalytic hydrogenation of the compound of formula (VIII) thus obtained to give the perindopril of formula (II).

The above process for the manufacture of perindopril would specifically avoid the use of harmful chemicals like phosgene or costly coupling agents like dicyclohexylcarbodiimide and 1-hydroxybenxotriazole usually used for such manufacture. The process would also not require any intervention of a catalyst and does not require any alkaline or acidic reaction conditions. Importantly, the process provides for manufacture of perindopril with high stereoselectively giving perindopril (II) having (S)-configuration in all the five chiral centres of the molecule, conforming to pharmacoepeial specifications.

The invention also relates to a method for preparation of the compound of formula (I) and also to a method for preparation of N-[(S)-1-carbethoxybutyl]-(S)-alanine of formula (III) used in the process.

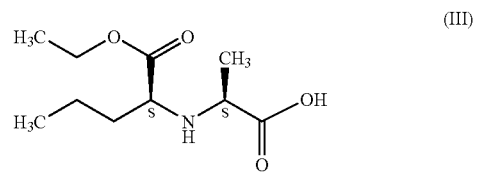

12 Claims, No Drawings

FOREIGN PATENT DOCUMENTS

| | | |
|---|---|---|
| EP | 0 129 461 | 12/1984 |
| EP | 0 309 324 | 3/1989 |
| EP | 1 256 590 | 11/2002 |
| EP | 1 279 665 | 1/2003 |
| GB | 2 095 252 | 9/1982 |
| WO | WO 96/33984 | 10/1996 |
| WO | WO 01/56353 | 8/2001 |
| WO | WO 01/56972 | 8/2001 |
| WO | WO 01/58868 | 8/2001 |

OTHER PUBLICATIONS

Hayashi et al. "Studies on angiotensin converting enzyme inhibitors. 4. Synthesis and angiotension converting enzyme inhibitory activites of 3-acyl-1-alkyl-2-oxoimidazolidine-4-carboxylic acid derivatives". *Journal of Medicinal Chemistry*, vol. 32, No. 2, pp. 289-297 (1989).

* cited by examiner

PROCESS FOR PREPARATION OF PERINDOPRIL AND SALTS THEREOF

This application is a 371 of PCT/IN03/00042 filed on Feb. 28, 2003.

FIELD OF THE INVENTION

The present invention relates to a novel process for preparation of perindopril of formula (II) and salts thereof

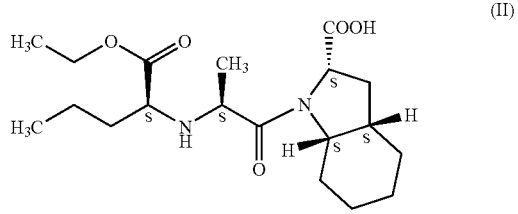

which is simple, convenient and cost-effective.

BACKGROUND OF THE INVENTION

The chemical entity (2S)-2-[(1S)-1-carbethoxybutylamino]-1-oxopropyl-(2S,3aS,7aS)-perhydroindole-2-carboxylic acid of formula (II), known generically as perindopril and its pharmaceutically acceptable salts, specially salt of perindopril with tertiary butyl amine i.e. perindopril erbumine are commercially valuable ACE Inhibitors, useful for the treatment of hypertension.

Vincent et. al. in U.S. Pat. No. 4,508,729 disclose a method for preparation of perindopril monoammonium salt, as a mixture of two diastereomers, involving reductive amination of (2S)-1-[(S)-alanyl]-2-carboxyperhydroindole with pyruvic acid in the presence of sodium cyanoborohydride. The (2S)-1-[(S)-alanyl]-2-carboxyperhydroindole, in turn is prepared by reaction of (2S)-2-ethoxycarbonylperhydroindole with L-BOC.-alanine to give (2S)-N-[(S)-BOC.-alanyl]-2-ethoxycarbonylperhydroindole, which on step-wise removal of the carboxyl and amino protecting groups gives (2S)-1-[(S)-alanyl]-2-carboxyperhydroindo. The synthesis is schematically represented hereinbelow.

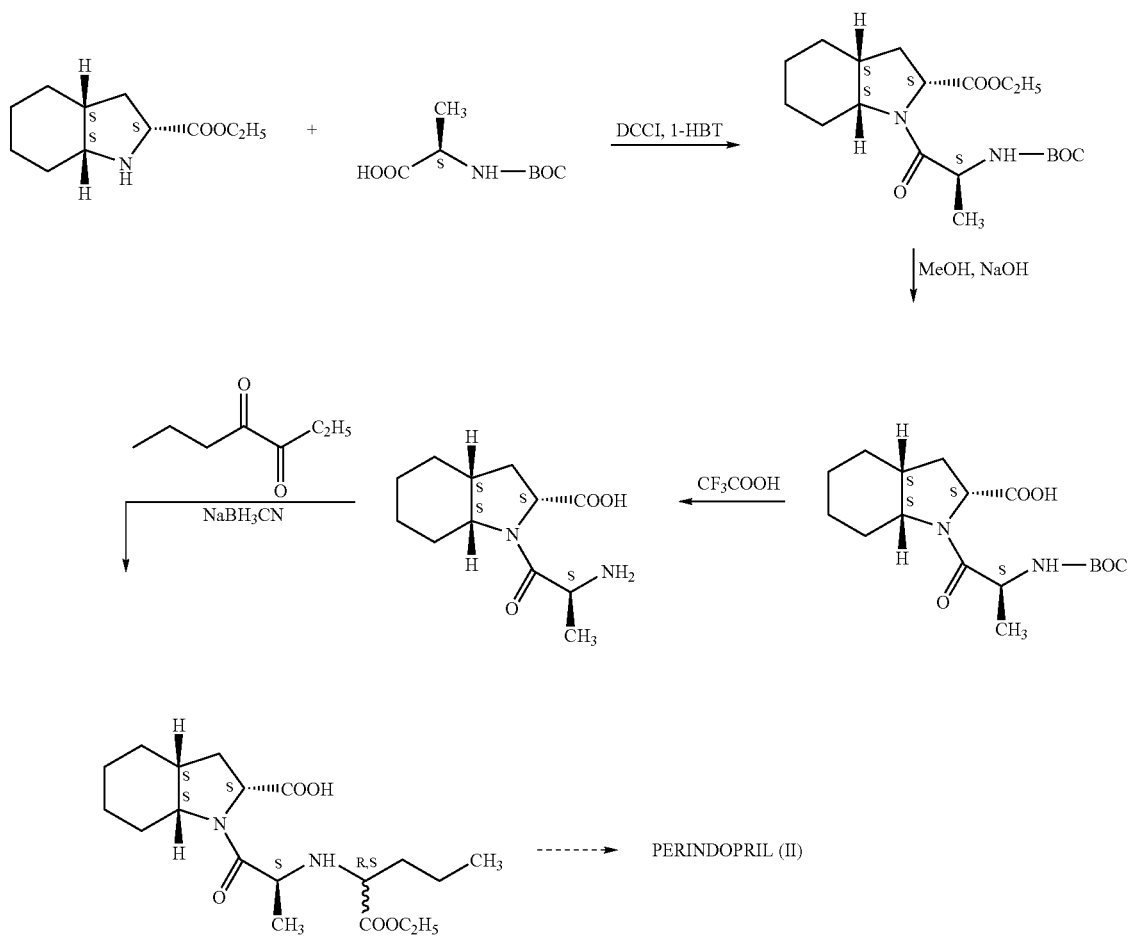

However, this method gives perindopril as a mixture of diastereomers and there are no enabling disclosure in the patent as to how the diastereomers are separated to give perindopril or its tert-butylamine salt i.e. perindopril erbumine having the desired (S) configuration for all the five chiral centers in the molecule. Moreover, the method involves protection of the amino group of the alanine moiety as the t-BOC group, which necessitates use of corrosive trifluoroacetic acid for its subsequent removal.

Vincent et. al. in U.S. Pat. No. 4,902,817 disclose a stereoselective process for the industrial synthesis of N-[(S)-1-carbethoxybutyl]-(S)-alanine comprising reaction of ethyl-L-norvalinate hydrochloride with pyruvic acid under catalytic hydrogenation conditions. The N-[(S)-1-carbethoxybutyl]-(S)-alanine thus obtained is a key intermediate for perindopril. The synthesis is schematically represented hereinbelow.

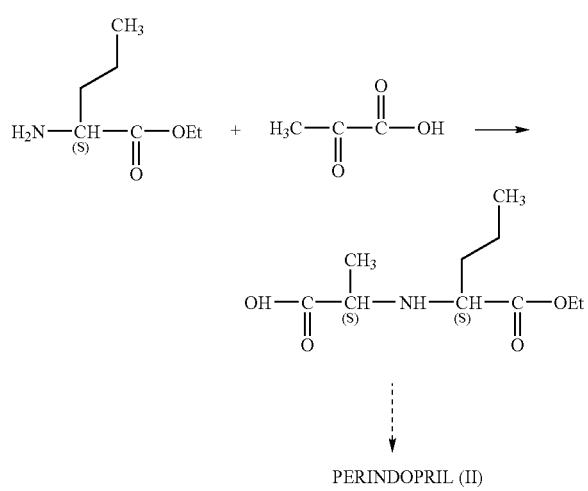

PERINDOPRIL (II)

Vincent et. al. in U.S. Pat. No. 4,914,214 disclose an industrial method for synthesis of perindopril erbumine comprising reacting ethyl or benzyl ester of (2S, 3aS,7aS)-2-carboxyperhydroindole with (S,S) diastereoisomer of N-[(S)-1-carbethoxybutyl]-(S)-alanine in an alkaline medium in the presence of a catalyst, such as dicyclohexylcarbodiimide in the presence of 1-hydroxybenzotriazole to give perindopril ethyl or benzyl ester. Subsequent deprotection and salt formation with tert-butyl amine gives perindopril erbumine.

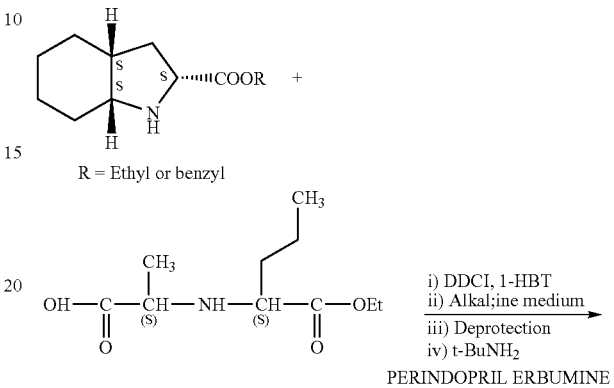

PERINDOPRIL ERBUMINE

Similar chemistry as disclosed in U.S. Pat. No. 4,914,214 is also embodied in Vincent et. al's. EP Patent No. 0 129 461.

Vincent et. al. in EP Patent No. 0 309 324 disclose yet another method for synthesis of (S,S) diastereoisomer of N-[(S)-1-carbethoxybutyl]-(S)-alanine, a key intermediate for perindopril comprising reaction of L-alanine benzyl ester p-toluenesulfonate with ammonia to form the free base, which is condensed with ethyl α-bromo valerate to give a racemic mixture of N-[(S)-1-carbethoxybutyl]-(S)-alanine and N-[(R)-1-carbethoxybutyl]-(S)-alanine. The (S) isomer is separated by resolution with maleic acid and subsequent removal of the benzyl ester group provides the (S,S) diastereoisomer of N-[(S)-1-carbethoxybutyl]-(S)-alanine, which can be further elaborated to perindopril and perindopril erbumine.

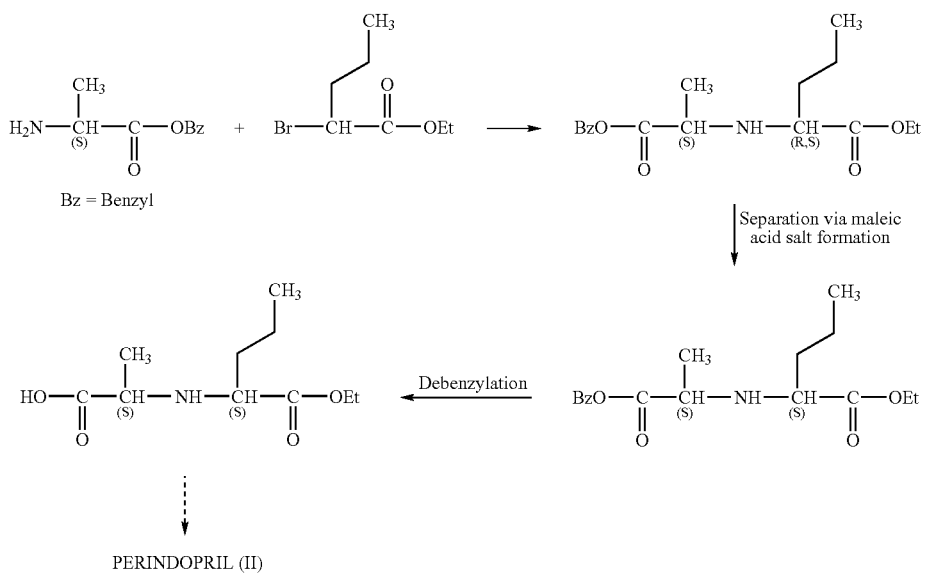

PERINDOPRIL (II)

Meizei et. al. in EP Patent No. 1 256 590 disclose a process for preparation of (2S, 3aS, 7aS)-1-(S)-alanyl-octahydro-1H-indole-2-carboxylic acid as an intermediate for perindopril comprising reaction of (2S)-2,3-dihydroindole-2-carboxylic acid with t-BOC-L-alanine to form the amide compound followed by hydrogenation to give (2S, 3aS, 7aS)-1-(S)-alanyl-octahydro-1H-indole-2-carboxylic acid, which can be further elaborated to perindopril.

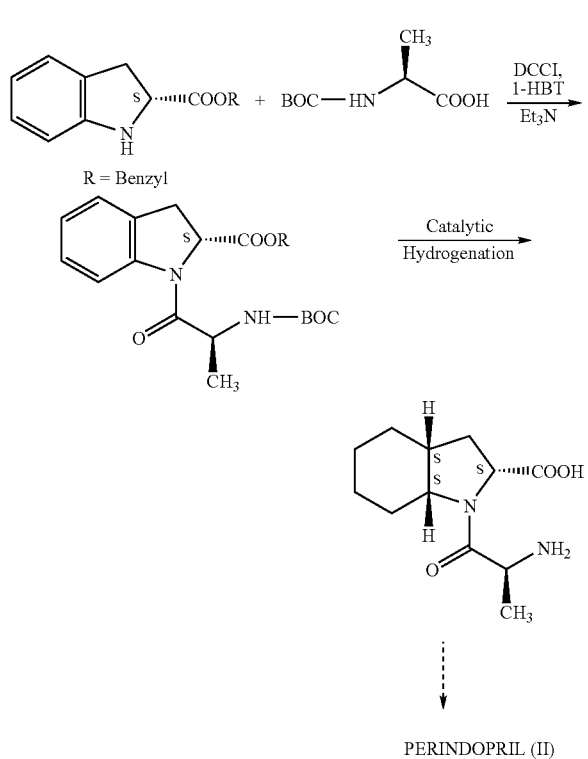

Souvie et. al. in published PCT Appln. No. WO 01/56353 disclose a method for preparation of the (S,S) diastereoisomer of N-[(S)-1-carbethoxybutyl]-(S)-alanine, a key intermediate for perindopril comprising reacting sodium pyruvate with L-norvalinate ester under reducing conditions using palladium carbon as catalyst.

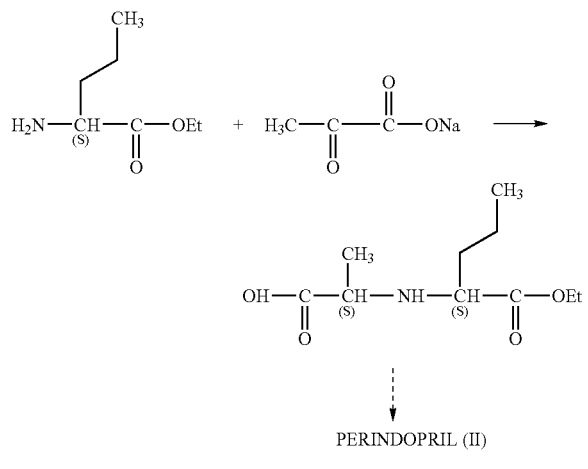

Souvie et. al. in published PCT Appln. No. WO 01/56972 disclose yet another method for preparation of the (S,S) diastereoisomer of N-[(S)-1-carbethoxybutyl]-(S)-alanine, a key intermediate for perindopril comprising reacting 1-alanine and ethyl 2-oxo-pentanoic acid under catalytic hydrogenation conditions and isolating the product at a pH between 3 to 3.5, followed by crystallization.

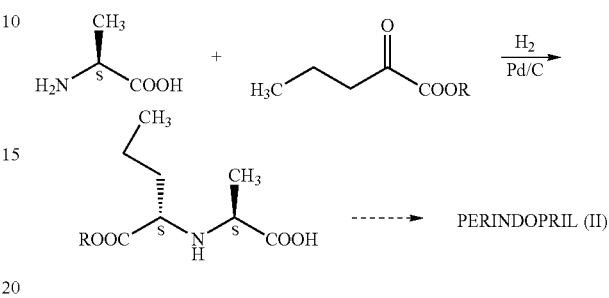

Langlois et. al. in published PCT Appln. No. WO 01/58868 disclose a further method for preparation of the (S,S) diastereoisomer of N-[(S)-1-carbethoxybutyl]-(S)-alanine, a key intermediate for perindopril comprising reacting benzyl ester of (2S, 3aS,7aS)-2-carboxyperhydroindole, p-toluene-sulfonate salt with (S,S) diastereoisomer of N-[(S)-1-carbethoxybutyl]-(S)-alanine in the presence of 0.4 to 0.6 moles of 1-hydroxybenzotriazole; 1 to 1.2 moles of dicyclohexylcarbodiimide and I mole of triethylamine at 77° C. to give the dipeptide compound, which on debenzylation gives perindopril.

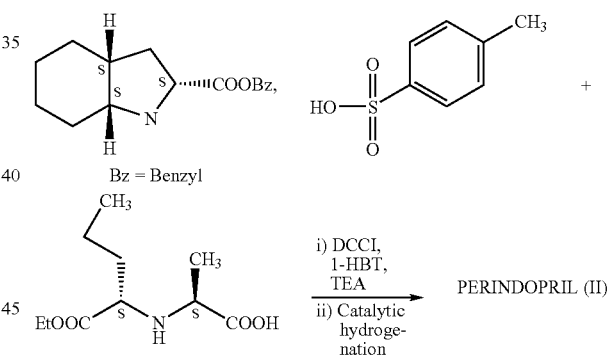

Serra et. al. in published PCT Appln. No. WO 96/33984 disclose N-sulfoxy anhydrides of N-[1-(S)-ethoxycarbonyl-3-phenylpropyl/butyl-S-alanine, and a process for preparation of several ACE inhibitors including perindopril using the said N-sulfoxy anhydride compounds. The N-sulfoxy anhydride is in turn prepared by reacting the corresponding carboxylic acid compound with N-(chlorosulfinyl)-heterocyclic compound, wherein the heterocycle is an alkyl imidazole, benzimidazole, tetrazole or other similar heterocyclic compounds.

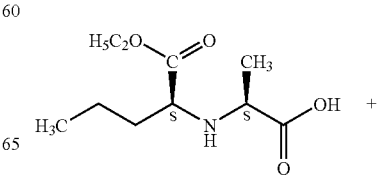

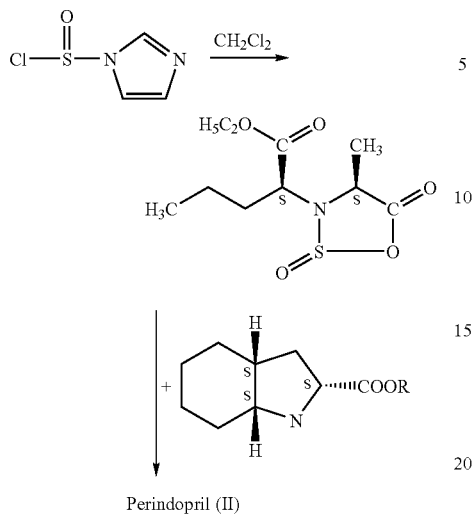

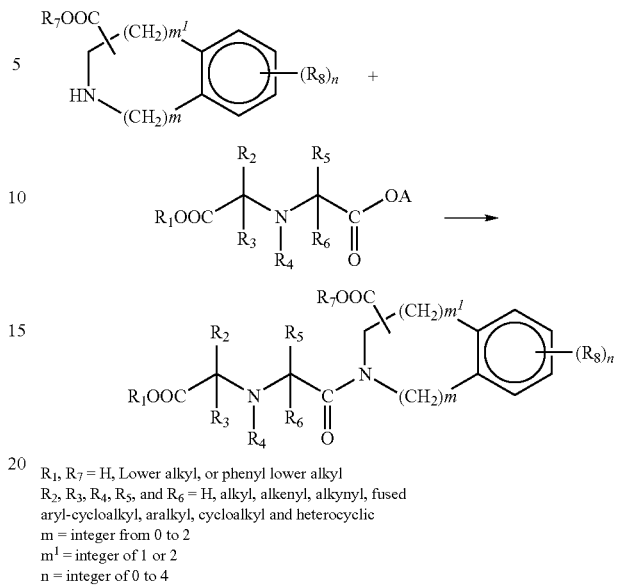

$R_1$, $R_7$ = H, Lower alkyl, or phenyl lower alkyl
$R_2$, $R_3$, $R_4$, $R_5$, and $R_6$ = H, alkyl, alkenyl, alkynyl, fused aryl-cycloalkyl, aralkyl, cycloalkyl and heterocyclic
m = integer from 0 to 2
$m^1$ = integer of 1 or 2
n = integer of 0 to 4

Cid et. al. in EP Patent No. 1 279 665 disclose N-carboxy anhydride of N-[1-(S)-ethoxycarbonyl-3-butyl-S-alanine, and a process for preparation of perindopril using the said N-carboxy anhydride compound.

However, this patent disclosure does not include perindopril as the antihypertensive and ACE Inhibitory compounds mentioned therein.

Palomo et. al. in DE Patent No: 197 21 290 describe a method for preparation of several ACE Inhibitors of formula (D), including perindopril, wherein Z is alkyl or phenyl and $R_1$ is an amino acid as found in commercially valuable ACE inhibitors. The process comprises the steps of first silylating the compound of formula (A) to give the (bis)silyl derivative of formula (B), followed by reaction of compound (B) with thionyl chloride to give the silylated acid chloride derivative of formula (C). Compound (C) is then reacted with the respective amino acid, $R_1H$ to give compound of formula (D).

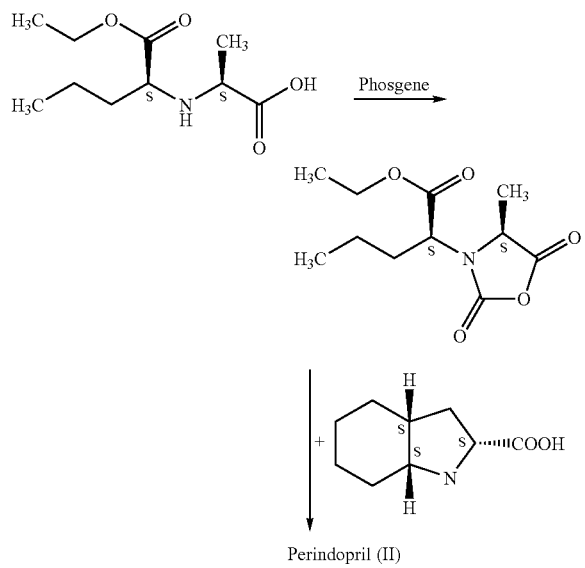

However, this method utilizes toxic and hazardous phosgene for preparation of the N-carboxy anhydride compound, thereby rendering it unsuitable for commercial manufacture.

Suh et. al. in GB Patent No. 2 095 252 claim certain N-(substituted aminoalkanoyl) heterocyclic compounds having antihypertensive and ACE Inhibition activity and a process for preparation thereof, which comprises an amide forming reaction of a suitable amine compound and the reactive derivatives of the suitable carboxylic acid compound. The reactive carboxylic derivatives mentioned therein include acyl halides, anhydrides, mixed anhydrides, lower alkyl esters, carbodiimides, carbonyl diimidazoles and the like.

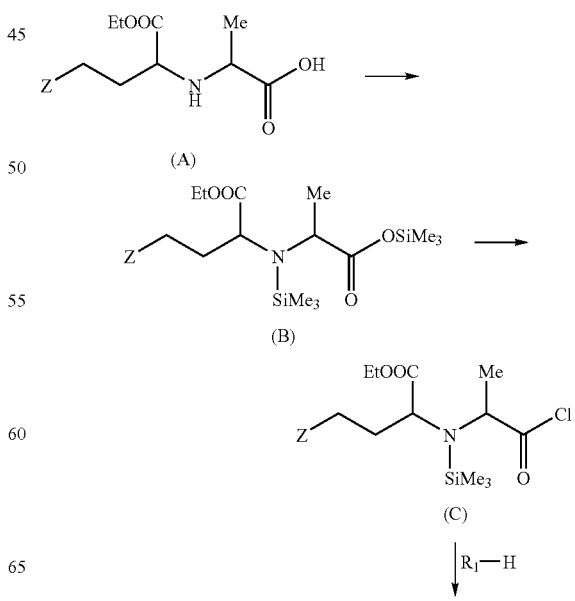

-continued

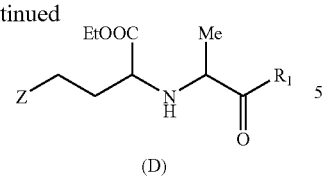

(D)

This method is however, lengthy and not cost-effective since there is a step of silylation using expensive silylating agents and subsequent step of desilylation involved.

It would be apparent from the above that while there are several known methods available for synthesis of perindopril, however, most of the methods either involve utilization of hazardous or costly coupling agents like dicyclohexylcarbodiimide and 1-hydroxybenzotriazole, toxic chemicals like phosgene or essentially require special acidic or alkaline conditions. These in turn lead to complexities in manufacture and render the methods to obtain such product less cost-effective.

OBJECTS OF THE INVENTION

It is thus the basic object of the present invention to provide a method for production of perindopril in a simple, safe, selective and cost-effective manner.

Yet another object of the present is to provide a novel method for preparation of perindopril, in high purity and which would be simple, safe, selective and cost-effective.

Yet further object is to provide a method of production of perindopril which would specifically avoid the use of harmful chemicals like phosgene or costly coupling agents like dicyclohexylcarbodiimide and 1-hydroxybenxotriazole used in the prior art.

Another object is to provide improved method of manufacture of perindopril which would not require any intervention of a catalyst and does not require any alkaline or acidic reaction conditions.

Yet farther object is directed to the improvement in manufacture of perindopril with high stereoselectively giving perindopril (II) having (S)-configuration in all the five chiral centres of the molecule, conforming to pharmacoepeial specifications.

SUMMARY OF THE INVENTION

In accordance with one aspect of the present invention there is provided a process for preparation of perindopril of formula (II) or its derivatives and/or pharmaceutically acceptable salts thereof,

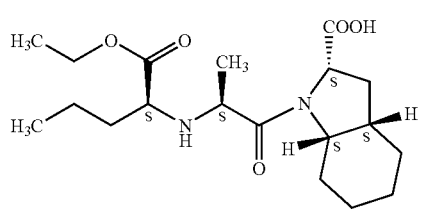

(II)

comprising reaction of compound of formula (I),

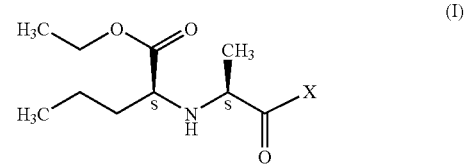

(I)

with compound of formula (VII)

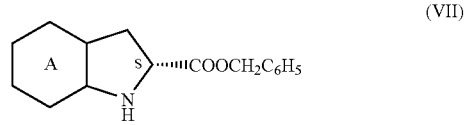

(VII)

wherein A signifies that the six-membered ring of the bicyclic system is either saturated or unsaturated to give compound of formula (VIII),

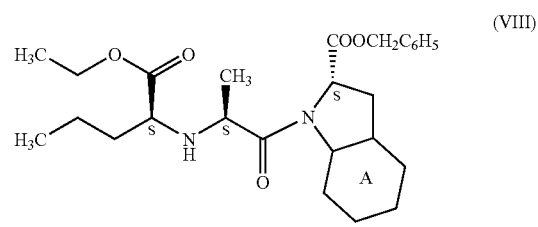

(VIII)

wherein A is as defined above, followed by catalytic hydrogenation of the compound of formula (VIII) thus obtained to give perindopril of formula (II).

In another aspect of the present invention there is provided a method for preparation of the compound of formula (I) comprising reaction of N-[(S)-1-carbethoxybutyl]-(S)-alanine of formula (III) with a halogenating agent.

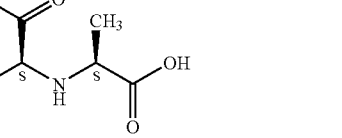

(III)

In yet another aspect of the present invention there is provided a novel method for preparation of N-[(S)-1-carbethoxybutyl]-(S)-alanine of formula (III)

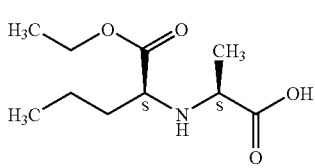

(III)

comprising the steps of reacting ethyl L-norvalinate of formula (IV)

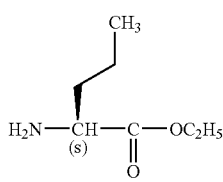

with anyone of racemic 2-halo propionic acid benzyl ester of formula (V) and optically active (R)-2-halo propionic acid benzyl ester of formula (V¹)

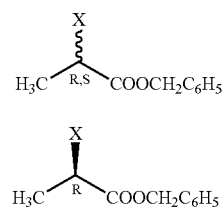

wherein X is chlorine or bromine in the presence of an organic solvent and in the presence of a base and obtaining therefrom the compound of formula (VI),

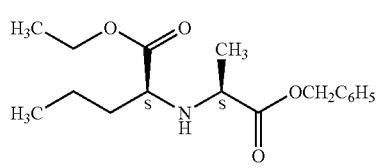

and removal of the benzyl protective group of said compound of formula (VI) through catalytic hydrogenation to give compound of formula (III),

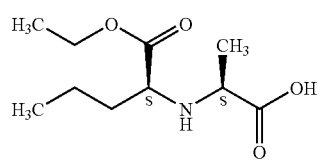

DETAILED DESCRIPTION OF THE INVENTION

All the abovementioned aspects of the present invention could be illustrated as detailed hereinbelow:

1) Preparation of N-[(S)-1-carbethoxybutyl]-(S)-alanine of Formula (III)

In one of the methods, ethyl-L-norvalinate of formula (IV), having (S)-configuration in the chiral carbon atom is reacted with racemic (±)-2-halo propionic acid benzyl ester of formula (V), wherein X is chlorine or bromine, in an organic solvent in the presence of an organic base under reflux conditions to give the benzyl ester of N-[-1-carbethoxybutyl]-(S)-alanine as a mixture of diastereomers i.e. a mixture of benzyl ester of N-[-1-carbethoxybutyl]-(S)-alanine and benzyl ester of N-[-1-carbethoxybutyl]-(R)-alanine.

The reaction can be carried out in any organic solvent in which both the reactants i. e. ethyl-L-norvalinate and racemic (±) 2-halo propionic acid benzyl ester are soluble. Typical of such solvents are nitrile solvents such as acetonitrile and propionitrile; chlorinated hydrocarbons such as dichloromethane, dichloroethane, chloroform and carbon tetrachloride; ketonic solvents such as methyl ethyl ketone, methyl isobutyl ketone and acetone; and aprotic solvents such as N,N-dimethylformamide and N,N-dimethylacetamide. Nitrile solvents are preferred and among these acetonitrile is the most preferred solvent.

The racemic (±) 2-halo propionic acid benzyl ester is employed in molar proportions of 1 to 1.5 moles per mole of ethyl-L-norvalinate, preferable in molar proportions of 1 to 1.2 moles per mole of ethyl-L-norvalinate.

The reaction is carried out in presence of organic bases such as diethylamine, triethylamine, pyridine, 2,3-diaminopyridine, 2,4-diaminopyridine, dicyclohexylamine, N-methyl morpholine etc. Among these, triethylamine is preferred. Typically, the base is employed in molar proportions of 1 to 5.0 moles per mole of ethyl-L-norvalinate, preferably in molar proportions of 1 to 3.0 moles per mole of ethyl-L-norvalinate.

At the end of the reaction, the organic solvent is evaporated off and the residue redissolved in a solvent and washed successively with an aqueous solution of an inorganic acid and an inorganic base.

The mixture of diastereomers obtained i.e. mixture of benzyl ester of N-[-1-carbethoxybutyl]-(S)-alanine and benzyl ester of N-[-1-carbethoxybutyl]-(R)-alanine can be separated by methods known in the art such as conventional chromatography, fractional crystallisation, crystallisation through formation of salts with organic salts such as methanesulfonic acid, p-toluenesulfonic acid, trifluoroacetic acid, trifluoromethanesulfonic acid, maleic acid, fumaric acid etc.

In a typical method of separation, a solution of the mixture of benzyl esters of N-[-1-carbethoxybutyl]-(S)-alanine and N-[-1-carbethoxybutyl]-(R)-alanine in an organic solvent is treated with the organic acid to facilitate the salt formation. To this is added a co-solvent and the solution kept aside to allow gradual crystallisation of the acid addition salt of the desired (S)-isomer, which is isolated by filtration to give benzyl ester of N-[-1-carbethoxybutyl]-(S)-alanine, acid addition salt in high optical purity.

Neutralisation of the salt with a base by methods known in the art affords the benzyl ester of N-[-1-carbethoxybutyl]-(S)-alanine of formula (VI) in high optical purity.

Solvents that can be employed for the salt formation and subsequent separation of the two isomers include inter alia nitrile solvents such as acetonitrile and propionitrile; chlorinated hydrocarbons such as dichloromethane, dichloroethane, chloroform and carbon tetrachloride; aliphatic ketonic solvents such as methyl ethyl ketone, methyl isobutyl ketone and acetone; cyclic ketones such as cyclopentanone and cyclohexanone; alkyl acetates such as methyl acetate and ethyl acetate; aliphatic hydrocarbons such as n-pentane, n-hexane and n-heptane; cyclic hydrocarbons such as cyclopentane and cyclohexane; aromatic hydrocarbons such as benzene, toluene and xylene.

Alternatively, ethyl-L-norvalinate of formula (IV), having (S)-configuration in the chiral carbon atom can be reacted with optically active (R)-2-halo propionic acid benzyl ester of formula (V¹), wherein X is chlorine or bromine in an organic solvent in the presence of an organic base under reflux conditions to give directly the benzyl ester of N-[-1-carbethoxybutyl]-(S)-alanine.

As in the case wherein racemic (±) 2-halo propionic acid benzyl ester of formula (V) is employed the reaction of ethyl-L-norvalinate and the with optically active (R)-2-halo propionic acid benzyl ester of formula (V¹) can be carried out in any organic solvent in which both the reactants i. e. ethyl-L-norvalinate and optically pure (R)-2-halo propionic acid benzyl ester are soluble. Typical of such solvents are nitrile solvents such as acetonitrile and propionitrile; chlorinated hydrocarbons such as dichloromethane, dichloroethane, chloroform and carbon tetrachloride; aliphatic ketonic solvents such as methyl ethyl ketone, methyl isobutyl ketone and acetone; cyclic ketones such as cyclopentanone and cyclohexanone; and aprotic solvents such as N,N-dimethylformamide and N,N-dimethylacetamide. Nitrile solvents are preferred and among these acetonitrile is the most preferred solvent.

The optically pure (R)-2-halo propionic acid benzyl ester is employed in molar proportions of 1 to 1.5 moles per mole of ethyl-L-norvalinate, preferable in molar proportions of 1 to 1.2 moles per mole of ethyl-L-norvalinate.

The reaction is carried out in presence of organic bases such as diethylamine, triethylamine, pyridine, 2,3-diaminopyridine, 2,4-diaminopyridine, dicyclohexylamine, N-methyl morpholine etc. Among these, triethylamine is preferred. Typically, the base is employed in molar proportions of 1 to 5.0 moles per mole of ethyl-L-norvalinate, preferably in molar proportions of 1 to 3.0 moles per mole of ethyl-L-norvalinate.

At the end of the reaction, the organic solvent is evaporated off and the residue redissolved in a solvent and washed successively with an aqueous solution of an inorganic acid and an inorganic base to give the benzyl ester of N-[-1-carbethoxybutyl]-(S)-alanine of formula (VI) in high optical purity.

The compound (VI) thus obtained by any of the two methods described hereinabove has an $[\alpha_D]^{20}$ of +47.5° (C=1; EtOH).

The benzyl protective group in compound (VI) thus obtained is then removed under catalytic hydrogenation conditions known in the art in the presence of Group VIII transition metal catalysts to give N-[(S)-1-carbethoxybutyl]-(S)-alanine of formula (III).

The catalysts are selected from palladium on carbon, palladium on alumina, palladium on barium carbonate, palladium on barium sulfate, palladium on calcium carbonate, palladium on kieselguhr (diatomaceous earth), palladium on silica-alumina, palladium on silica-gel, palladium on strontium carbonate, palladium on tin oxide, palladium on titania, palladium hydroxide on carbon, platinum on carbon, platinum dioxide, platinum on alumina, platinum on barium carbonate, platinum on barium sulfate, platinum on calcium carbonate, platinum on kieselguhr (diatomaceous earth), platinum on silica-alumina, platinum on silica-gel, platinum on strontium carbonate, platinum on tin oxide, platinum on titania, iridium on carbon, iridium on alumina powder, rhodium on carbon, rhodium hydroxide on carbon, rhodium on alumina, rhodium on kieselguhr (diatomaceous earth), rhodium on silica-alumina, rhodium on silica-gel, rhodium on titania, ruthenium on carbon, ruthenium on alumina, ruthenium on kieselguhr (diatomaceous earth), ruthenium on silica-alumina, ruthenium on silica-gel, rhodium on titania, rhenium on carbon, rhenium on alumina, rhenium on kieselguhr (diatomaceous earth), rhenium on silica-alumina, rhenium on silica-gel, rhenium on titania etc. The aforesaid Group VIII metal catalyst are employed either in the inactivated form or in the activated forms. In addition, suitable forms in which the catalysts are employed include powder, granules, extrudate, pellets and spheres.

The hydrogenation of compound (VI) is carried out in an organic solvent or a mixture of organic solvent and water. Typical solvents include alcohols such as methanol and ethanol; aliphatic ketonic solvents such as acetone, methyl ethyl ketone and methyl isobutyl ketone; cyclic ketones such as cyclopentanone and cyclohexanone; ether solvents such as tetrahydrofuran, diethyl ether, diisopropyl ether, glyme and diglyme, aliphatic hydrocarbons such as n-pentane, n-hexane and n-heptane; cyclic hydrocarbons such as cyclopentane and cyclohexane. Alcohols are preferred and among alcohols ethanol is the most preferred solvent.

At the end of the reaction, the catalyst is filtered off and evaporation of the solvent gives compound of formula (III) of high optical purity. Optionally, the compound (III) can be further purified by crystallisation from any of the aforesaid solvents or mixtures thereof before use in the next step.

The starting materials used in the synthesis, viz. ethyl-L-norvalinate of formula (IV), racemic (±) 2-halo propionic acid benzyl ester of formula (V) and with optically active (R)-2-halo propionic acid benzyl ester of formula (V¹) can be prepared by method known in the art or can be procured from commercial sources. Both 2-chloro and 2-bromo propionic acid benzyl esters can be used in the synthesis.

2) Preparation of N-[(S)-1-carbethoxybutyl]-(S)-alanine carboxylic acid halide (I)

The N-[(S)-1-carbethoxybutyl]-(S)-alanine of formula (III) obtained in the previous step is then converted into the carboxylic acid halide i.e. N-[(S)-1-carbethoxybutyl]-(S)-alanine carboxylic acid halide of formula (I), wherein X is chlorine or bromine by reaction with a halogenating agent known in the art in a suitable anhydrous organic solvent in the presence of or absence of an inert gas.

The carboxylic acid halide (I) can be formed by reaction of the carboxylic acid derivative (III) by employing procedures as the case of a general synthesis described in GB Patent No. 2 095 252 and U.S. Pat. No. 4,760,162.

The carboxylic acid halide formation can be effected by reaction of the carboxylic acid derivative (III) with a halogenating agent selected from thionyl chloride, thionyl bromide, sulfuryl chloride, phosphorous trichloride, phosphorous tribromide, phosphorous pentachloride, phosphorous pentabromide, phosphorous oxychloride, oxalyl chloride etc.

Typically, the carboxylic acid derivative (III) is reacted with the halogenating agent in an organic solvent to form the corresponding acid halide (I). For instance, a solution of the carboxylic acid derivative (III) in an organic solvent can be reacted with thionyl chloride, thionyl bromide, sulfuryl chloride, phosphorous trichloride, phosphorous tribromide, phosphorous pentachloride, phosphorous pentabromide, phosphorous oxychloride or oxalyl chloride to form the acid halide (I).

Thus, in accordance with a specific embodiment of the present invention the N-[(S)-1-carbethoxybutyl]-(S)-alanine of formula (III) obtained in the previous step is dissolved in an anhydrous organic solvent is reacted with phosphorous pentachloride and the reaction mixture agitated at a temperature ranging from −20° C. to about +30° C. till completion of the reaction. At the end of the reaction, the solvent is evaporated off to give the N-[(S)-1-carbethoxybutyl]-(S)-alanine carboxylic acid chloride of formula (I).

Solvents that can be used for formation of the carboxylic acid halide (I) include chlorinated hydrocarbons such as dichloromethane and dichloroethane, aliphatic non-polar solvents such as hexane, heptane, cyclohexane or cycloheptane, and aromatic hydrocarbons such as benzene and toluene. The solvent has to be anhydrous, meaning whereby the water content in the solvent should be as low as possible.

The reaction can be conducted in the presence of an inert gas such as nitrogen and argon or in the absence of an inert gas atmosphere. Both the conditions do not produce any appreciable variations in the yield and purity of the carboxylic acid halide (I) obtained.

The halogenating agent is employed in molar proportions of 1.0 to 5.0 moles per mole of the N-[(S)-1-carbethoxybutyl]-(S)-alanine of formula (III) used.

The reaction can be carried out in ambient temperatures ranging from −20° C. to about +30° C., the preferred temperature is between 20° C. to 25° C.

The reaction is normally complete in 1 to 6 hours depending on the solvent employed and the temperature of the reaction.

The N-[(S)-1-carbethoxybutyl]-(S)-alanine carboxylic acid halide of formula (I) thus formed can be isolated by evaporation off the solvent or the solution of the same in the organic solvent can be used without isolation in the next step leading to production of perindopril. The compound is found to be stable at low temperatures and can be stored either in the solid form or in the solution form under an atmosphere of an inert gas and in the absence of moisture.

3) Preparation of Perindopril of Formula (II)

The N-[(S)-1-carbethoxybutyl]-(S)-alanine carboxylic acid halide of formula (I) is reacted with benzyl ester of the bicyclic compound of formula (VII), wherein A signifies that the six-membered ring of the bicyclic system is either saturated or unsaturated, For instance, when A signifies that the six-membered ring is saturated, the compound (VII) is the benzyl ester of (2S, 3aS, 7aS)-2-carboxyperhydroindole, which can be represented by formula (VII-A), and when A signifies that the six-membered ring is unsaturated, the compound (VII) is the benzyl ester of indoline-2(S)-carboxylic acid, which can be represented by formula (VII-B). The reaction of compound (I) with compound (VII-A) or (VII-B) is carried out in an organic solvent at low to ambient temperature and in the presence of a base to facilitate formation of the peptide bond and thereby give compound of formula (VIII), wherein A has the same meaning as defined hereinabove.

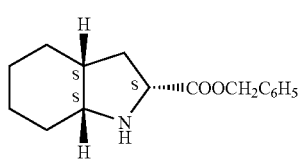

(VII-A)

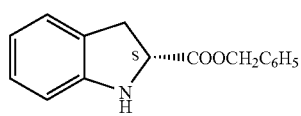

(VII-B)

The benzyl ester of (2S, 3aS, 7aS)-2-carboxyperhydroindole of formula (VII-A) is a known compound can be prepared in accordance with the methods disclosed in U.S. Pat. Nos. 4,508,749, 4,879,392, 4,935,525, 5,258,525, EP Patent No. 0 037 231, EP Patent No. 0 084 164, EP Patent No. 0 115 345, EP Patent No. 0 173 199, and EP Patent No. 0 132 580.

Similarly, the benzyl ester of indoline-2(S)-carboxylic acid (VII-B) is also known compound and can be prepared in accordance with the methods disclosed in U.S. Pat. No. 4,914,214.

The reaction of compound (I) with either compound (VII-A) or (VII-B) can be conducted in organic solvents, preferably anhydrous solvents, selected from chlorinated hydrocarbons such as dichloromethane and dichloroethane; aromatic hydrocarbons such as benzene and toluene; aliphatic hydrocarbons such as hexane, heptane, cyclopentane and cyclohexane. Of all the solvents chlorinated hydrocarbons are preferred.

The reaction can be carried out at low to ambient temperatures ranging from −20° C. to +30° C., preferably between −10° C. to −15° C. The reaction is complete in 30 mns to 2 hours depending on the temperature employed.

The reaction is carried out in presence of organic bases such as diethylamine, triethylamine, pyridine, 2,3-diaminopyridine, 2,4-diaminopyridine, dicyclohexylamine, N-methyl morpholine etc. Among these, triethylamine is preferred. Typically, the base is employed in molar proportions of 1 to 5.0 moles per mole of compound (VII-A), preferably in molar proportions of 1 to 3.0 moles per mole of compound (VII-A).

The molar proportion of the benzyl ester of (2S, 3aS, 7aS)-2-carboxyperhydroindole of formula (VII-A) and benzyl ester of indoline-2(S)-carboxylic acid (VII-B) employed can be between 0.85 to 0.90 moles per mole of the, preferably between 0.85 to 0.90 moles per mole of compound of formula (I).

The benzyl ester of compound of formula (VIII), thus obtained by reaction of compound of formula (I) and compound of formula (VII-A), wherein A signifies that the six-membered ring of the bicyclic system is saturated can be isolated by evaporation of the organic solvent, or preferably the solution containing the same, without isolation can be used for catalytic hydrogenation, whereby the benzyl protective group is cleaved to give perindopril of formula (II).

Similarly, the benzyl ester of compound of formula (VIII) thus obtained by reaction of compound of formula (I) and compound of formula (VII-B), wherein A signifies that the six-membered ring of the bicyclic system is unsaturated can be isolated by evaporation of the organic solvent, or preferably the solution containing the same, without isolation can be used for catalytic hydrogenation, with concurrent reduction of the aromatic ring and benzylation to give perindopril of formula (II).

The benzyl protective group in compound (VIII), thus obtained, wherein A signifies that the six-membered ring of the bicyclic system is saturated can then be removed under catalytic hydrogenation conditions known in the art in the presence of Group VIII transition metal catalysts to give perindopril of formula (II).

Similarly, the benzyl protective group and the aromatic ring in compound (VIII), thus obtained, wherein A signifies that the six-membered ring of the bicyclic system is unsaturated can then be removed concurrently under catalytic hydrogenation conditions known in the art in the presence of Group VIII transition metal catalysts to give perindopril of formula (II).

The catalysts are selected from palladium on carbon, palladium on alumina, palladium on barium carbonate, palladium on barium sulfate, palladium on calcium carbonate, palladium on kieselguhr (diatomaceous earth), palladium on silica-alumina, palladium on silica-gel, palladium on strontium carbonate, palladium on tin oxide, palladium on titania, palladium hydroxide on carbon, platinum on carbon, platinum dioxide, platinum on alumina, platinum on barium carbonate, platinum on barium sulfate, platinum on calcium carbonate, platinum on kieselguhr (diatomaceous earth), platinum on silica-alumina, platinum on silica-gel, platinum on strontium carbonate, platinum on tin oxide, platinum on titania, iridium on carbon, iridium on alumina powder, rhodium on carbon, rhodium hydroxide on carbon, rhodium on alumina, rhodium on kieselguhr (diatomaceous earth), rhodium on silica-alumina, rhodium on silica-gel, rhodium on titania, ruthenium on carbon, ruthenium on alumina, ruthenum on kieselguhr (diatomaceous earth), ruthenium on silica-alumina, ruthenium on silica-gel, rhodium on titania, rhenium on carbon, rhenium on alumina, rhenium on kieselguhr (diatomaceous earth), rhenium on silica-alumina, rhenium on silica-gel, rhenium on titania etc. The aforesaid metal catalyst are employed either in the inactivated form or in the activated forms. In addition, suitable forms in which the catalysts are employed include powder, granules, extrudate, pellets and spheres.

The hydrogenation of compound (VIII), wherein A signifies that the six-membered ring of the bicyclic system is saturated or unsaturated can be conducted in an organic solvent or a mixture of organic solvents or an in an organic solvent or a mixture of organic solvents in admixture with water. Typical solvents include alcohols such as methanol and ethanol; aliphatic ketonic solvents such as acetone, methyl ethyl ketone and methyl isobutyl ketone; cyclic ketones such as cyclopentanone and cyclohexanone; ether solvents such as tetrahydrofuran, diethyl ether, diisopropyl ether, glyme and diglyme, aliphatic hydrocarbons such as n-pentane, n-hexane and n-heptane; cyclic hydrocarbons such as cyclopentane and cyclohexane and aromatic hydrocarbons such as benzene and toluene. Alcohols and aromatic hydrocarbons are preferred and among alcohols ethanol is the most preferred solvent and among aromatic hydrocarbons toluene is the most preferred solvent.

At the end of the reaction, the catalyst is filtered off and evaporation of the solvent gives perindopril (II) of high optical purity conforming to pharmacoepaeial specifications. Optionally, the compound (II) can be further purified by crystallisation from any of the aforesaid solvents or mixtures thereof before converting into the physiologically acceptable erbumine salt.

Of the two methods described hereinabove, the preparation of perindopril (II) by condensation of N-[(S)-1-carbethoxybutyl]-(S)-alanyl halide of formula (I) with (2S, 3aS, 7aS)-2-carboxyperhydroindole of formula (VII-A), followed by catalytic hydrogenation is most preferred.

The erbumine salt formation of perindopril (II) can be carried out by any of the known methods disclosed in U.S. Pat. No. 4,914,214 and PCT Appln. published as WO 01/58868. The perindopril erbumine thus obtained can further be crystallised to afford the α-crystalline form as disclosed in PCT Appln. published as WO 01/87835, the β-crystalline form as disclosed in PCT Appln. published as WO 01/87836, or the γ-crystalline form as disclosed in PCT Appln. published as WO 01/83439.

The synthesis of perindopril of formula (II) in accordance with the present invention is schematically summarized in Scheme-I.

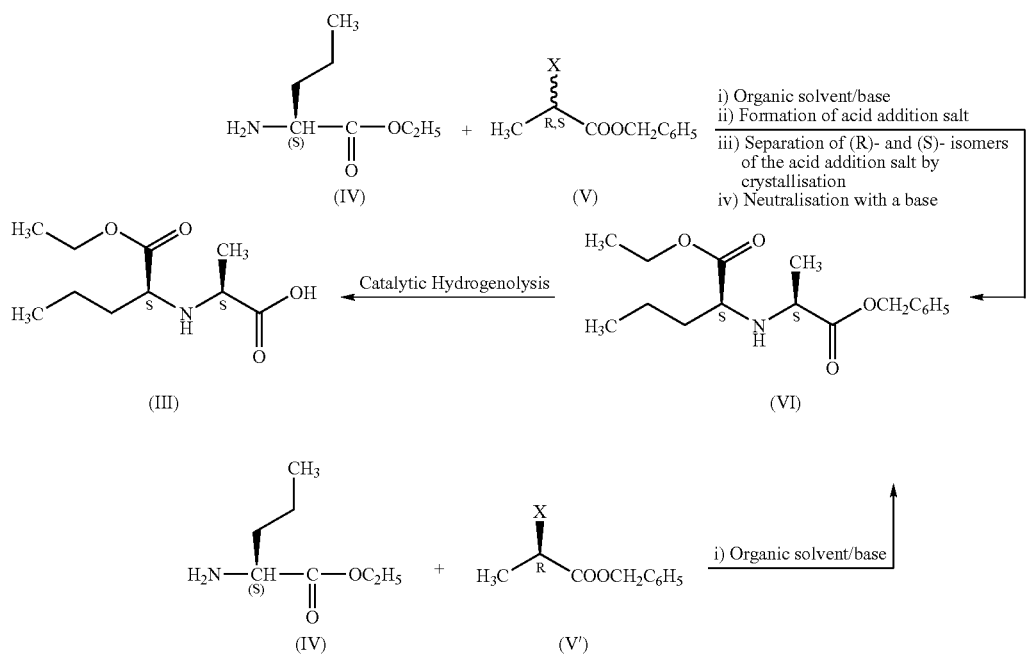

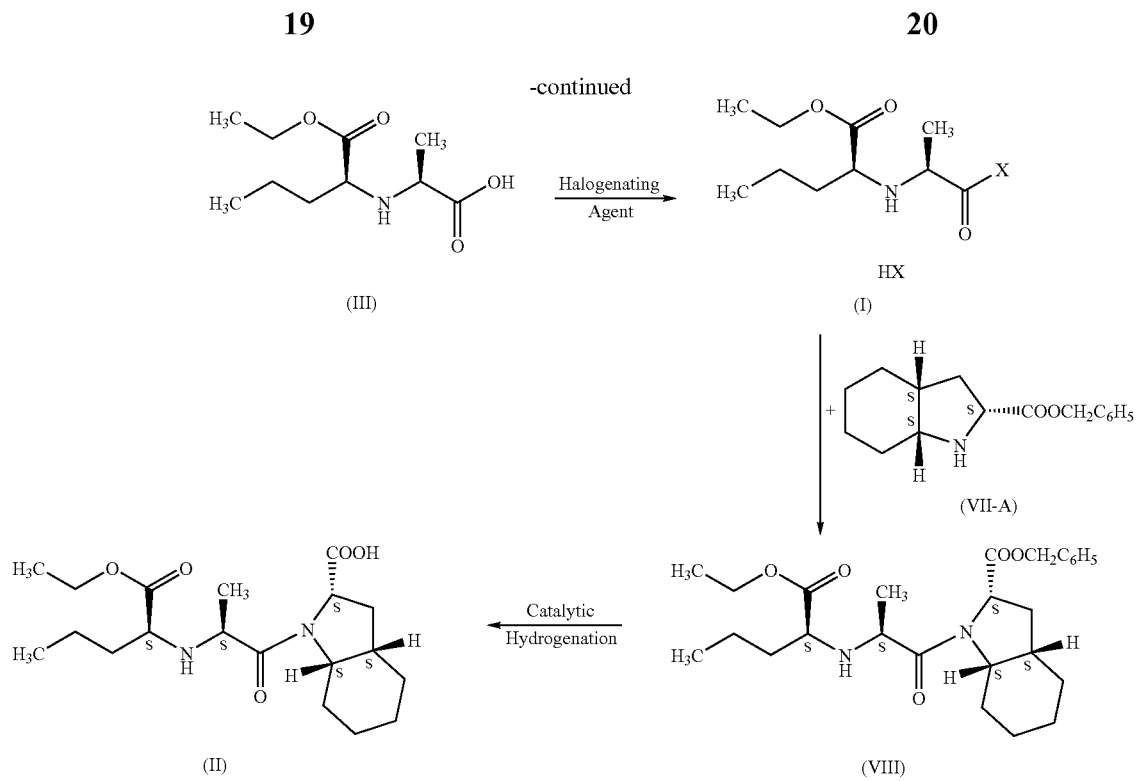

It is to be understood all the variations in the process form a part of the embodiment of the present invention and no enabling description of the invention as shown in the Examples provided hereinbelow should be construed as limiting the scope and spirit of the present invention.

EXAMPLE-1

Preparation of N-[1-(S)-ethoxycarbonyl-1-butyl]-(S)-alanine (III)

Step I: Preparation of N-[1-(S)-ethoxycarbonyl-1-butyl]-(R, S)-alanine benzyl ester To a solution of ethyl-L-norvalinate (IV, 62 g, 0.427 moles) in acetonitrile (300 ml) were added successively racemic (±)-benzyl-2-bromo-propionate (V, 125 g, 0.514 moles) and triethyl amine (178 ml, 1.282 moles). The reaction mixture was refluxed for 7-8 hrs. The excess solvent was removed by distillation under reduced pressure to afford a thick oil. The oil was dissolved in a mixture of diisopropyl ether (500 ml) and water (250 ml). The organic phase was extracted in 10% hydrochloric acid solution (250 ml×2). The combined acidic extracts were made alkaline by addition of an aqueous solution of sodium carbonate. The aqueous phase was again extracted with diisopropyl ether (200 ml×2). The combined organic layer was concentrated under reduced pressure to afford 103 g of the title compound as an oil.

IR: 1758 & 1728 cm$^{-1}$

PMR (CDCl$_3$, δ): 0.65-1.5 (m, 13H, 2 X —CH$_3$, C$_3$H$_7$); 2.00 (s, 1H, —NH—); 2.90-3.55 (m, 2 X —CH—); 3.85 (q, 2H, —CH$_2$—); 5.2 (s, 2H, —CH$_2$—); 7.3 (m, 5H, ArH).

Step II: Preparation of Maleate Salt of N-[1-(S)-ethoxycarbonyl-1-butyl]-(S)-alanine benzy lester To a solution of the oil obtained in Step I (100 g, 0.325 moles) in acetone (250 ml) was added maleic acid (22.67 g, 0.195 moles). The solution was agitated and to it was added cyclohexane (600 ml). The reaction mixture was heated under reflux for 2.5-2 hrs, and then cooled gradually to 22-25 C and then further to 0-5 C. The solid crystallizing out was collected by filtration and dried at 45-50 C under reduced pressure to give 42 g of maleate salt of N-[1-(S)-ethoxycarbonyl-1-butyl]-(S)-alanine benzyl ester. Recrystallization from a mixture of acetone and cyclohexane gave 38 g of the product having desired optical purity.

[α$_D^{20}$]: 18.8 (C=1/EtOH)

Melting point: 100 C.

PMR (CDCl$_3$, δ): 0.95 (t, 3H, —CH$_3$); 1.25 (t, 3H, —CH$_3$); 1.5 (bq, 2H, —CH$_2$—); 1.6 (d, 3H, —CH$_3$); 1.8 (q, 2H, —CH$_2$—); 3.6 (t, 1H, —CH—); 3.8 (q, 1H, —CH—); 4.25 (q, 2H, —CH$_2$—); 5.25 (s, 1H, —CH$_2$—); 6.25 (s, 2H, —CH—); 7.30 (s, 5H, ArH); 9.00 (bs, 3H, —NH—, —COOH).

Step III: Preparation of N-[1-(S)-ethoxycarbonyl-1-butyl]-(S)-alanine benzyl ester (VI)

To a suspension of the maleate salt obtained in Step II (23 g) in water (100 ml) and dichloromethane (200 ml), was added aqueous ammonia solution (25%) till pH of the reaction mixture remained constant in the range of 8.5-9.0. The organic layer was separated and concentrated in vacuum to afford 16 g the title compound as an oil.

[α$_D^{20}$]: 47.5 (C=1/EtOH)

PMR (CDCl$_3$, δ): 0.95 (t, 3H, —CH$_3$); 1.25 (t, 3H, —CH$_3$); 1.5 (bq, 2H, —CH$_2$—); 1.6 (d, 3H, —CH$_3$); 1.8 (q, 2H, —CH$_2$—); 3.6 (t, 1H, —CH—); 3.8 (q, 1H, —CH—); 4.25 (q, 2H, —CH$_2$—); 5.25 (s, 1H, —CH$_2$—); 7.30 (s, 5H, ArH); 9.00 (bs, H, —NH—).

Step IV: Preparation of N-[1-(S)-ethoxycarbonyl-1-butyl]-(S)-alanine (III)

A solution of the oil obtained in Step III (14.5 g) in absolute ethanol (150 ml) was hydrogenated in the presence of 10% palladised charcoal (0.8 g) under 40-45 psi pressure for 1.5-2 hrs. The reaction mixture was then concentrated under reduced pressure to afford a solid. This was dried at 40-45 C under vacuum to give 8.7 g of the title compound.

[$\alpha_D^{20}$]: 4.6 (C=1/EtOH)

Melting point: 148 C

PMR (DMSO-$d_6$, δ): 0.9 (t, 3H, —$CH_3$); 1.15 (t, 6H, 2 X —$CH_3$); 1.2-1.4 (m, 2H, —$CH_2$—); 1.45-1.6 (m, 2H, —$CH_2$—); 3.0-3.3 (m, 2H, 2 X —CH—); 4.0-4.2 (q, 2H, —$CH_2$—).

EXAMPLE-2

Preparation of N-[1-(S)-ethoxycarbonyl-1-butyl]-(S)-alanine (III)

Step I: Preparation of N-[1-(S)-ethoxycarbonyl-1-butyl]-(S)-alanine benzyl ester To a solution of ethyl-L-norvalinate (IV, 62 g, 0.427 moles) in acetonitrile (300 ml) were added successively benzyl-(R)-2-bromo-propionate ($V^1$, 20 g, 0.0822 moles) and triethyl amine (28 ml, 0.2016 moles). The reaction mixture was refluxed for 7-8 hrs. The excess solvent was removed by distillation under reduced pressure to afford a thick oil. The oil was dissolved in a mixture of diisopropyl ether (80 ml) and water (40 ml). The organic phase was extracted in 10% hydrochloric acid solution (40 ml×2). The combined acidic extracts were made alkaline by addition of an aqueous solution of sodium carbonate. The aqueous phase was again extracted with diisopropyl ether (200 ml×2). The combined organic layer was concentrated under reduced pressure to afford 103 g of the title compound as an oil.

IR: 1758 & 1728 $cm^{-1}$

PMR ($CDCl_3$, δ): 0.65-1.5 (m, 13H, 2 X —$CH_3$, $C_3H_7$); 2.00 (s, 1H, —NH—); 2.90-3.55 (m, 2 X—CH—); 3.85 (q, 2H, —$CH_2$—); 5.2 (s, 2H, —$CH_2$—); 7.3 (m, 5H, ArH).

Step-II: Preparation of N-[1-(S)-ethoxycarbonyl-1-butyl]-(S)-alanine (III)

A solution of N-[1-(S)-ethoxycarbonyl-1-butyl]-(S)-alanine benzyl ester (14.5 g, as obtained in Step-I) in ethanol (150 ml) was hydrogenated in the presence of 10% palladised charcoal (0.8 g) under 40-45 psi hydrogen pressure for 1.5 to 2 hrs. The reaction mixture was concentrated under reduced pressure to give an oil. Crystallization from a mixture of acetonitrile and ethanol (1:3) gave 6.1 g the title compound

[$\alpha_D^{20}$]: 4.6 (C=1/EtOH)

Melting point: 148 C

PMR (DMSO-$d_6$, δ): 0.9 (t, 3H, —$CH_3$); 1.15 (t, 6H, 2 X —$CH_3$); 1.2-1.4 (m, 2H, —$CH_2$—); 1.45-1.6 (m, 2H, —$CH_2$—); 3.0-3.3 (m, 2H, 2 X —CH—); 4.0-4.2 (q, 2H, —$CH_2$—).

EXAMPLE-3

Preparation of N-[1-(S)-ethoxycarbonyl-1-butyl]-(S)-alanyl chloride (I)

To a slurry of N-[1-(S)-ethoxycarbonyl-1-butyl]-(S)-alanine (III, 1.5 g, 0.0069 moles) in n-hexane (10 ml) was purged dry hydrogen chloride gas at 25-30° C. under agitation. To this was added finely grounf phosphorous pentachloride (1.8 g, 0.0086 moles) in four lots, each after an interval of 10 mns. After the complete addition the reaction mixture was agitated for 1.5 hrs. The solid precipitated was filtered, washed with hexane to give 1.88 g of the title compound (I).

IR ν $cm^{-1}$: 1741 and 1791

PMR (DMSO-$d_6$, δ): 0.90 (3H, t, —$CH_3$); 1.15 (3H, t, —$CH_3$); 1.2-1.5 (5H, m, —$CH_2$, —$CH_3$); 1.5-1.9 (2H, m, —$CH_2$); 3.8-4.3 (4H, m, 2X—CH, —$CH_2$); 9.6 (1H, bs, —NH).

EXAMPLE-4

Preparation of Perindopril (II)

Step I: Preparation of Perindopril benzyl ester (VIII)

To a solution of (2S, 3aS, 7aS0-octahydroindole-2-carboxylic acid benzyl ester (VII-A, 1.6 g, 0.0062 moles) and triethylamine (2.9 ml, 0.0208 moles) in dichloromethane (10 ml) was added a slurry of N-[1-(S)-ethoxycarbonyl-I-butyl]-(S)-alanyl chloride (I, 1.88 g. 0.0069 moles) in dichloromethane 910 ml) at −10 to 15° C. over a period of 25-30 mns.

After the complete addition the reaction temperature was gradually raised to 25-30° C. The reaction mixture was quenched with water (20 ml). The organic layer was separated, washed successively with 55 Hcl (10 ml×2 times), 105 aqueous sodium carbonate solution (10 ml×2 times) and water 910 ml×2 times). The organic layer was concentrated under reduced pressure at 40-45° C. to give 2.3 g of the benzyl ester (VIII).

Step II: Preparation of Perindopril (II)

Perindopril benzyl ester (1.4 g) obtained in Step I was dissolved in absolute ethanol (15 ml). To the solution was added 10% Pd-C (5% w/w) and the mixture hydrogenated at 20-22° C. for 3 hours till completion of the reaction. The catalyst was filtered off and the filtrate concentrated under reduced pressure at 45° C. to give 1.3 g of perindopril (II).

The method of synthesis of perindopril in accordance with the present invention as discussed and illustrated above offers various advantages over the prior art methods including:

a) unlike the reaction of N-carboxyanhydride N-[(S)-1-carbethoxybutyl]-(S)-alanine and (2S, 3aS, 7aS)-2-carboxyperhydroindole (VII-A), wherein the carboxyanhydride used is prepared using hazardous and toxic chemicals like phosgene the acid halides used in the process of the invention can be prepared easily without use of any hazardous compounds and once formed can be used as such for reaction with the bicyclic compound for obtaining perindopril.

b) unlike the reaction of N-[(S)-1-carbethoxybutyl]-(S)-alanine and (2S, 3aS, 7aS)-2-carboxyperhydroindole (VII-A), the reaction with the acid halide (I) used in the present process can be carried out in the absence of toxic, hazardous and costly coupling agents like dicyclohexylcarbodiimide and 1-hydroxybenxotriazole, c) unlike the reaction of N-[(S)-1-carbethoxybutyl]-(S)-alanine and (2S, 3aS, 7aS)-2-carboxyperhydroindole (VII-A), the reaction with the acid halide (I) used in the process of the invention does not require any intervention of a catalyst and does not require any alkaline or acidic reaction conditions, d) the condensation reaction followed in the process of the invention is highly stereoselective, giving perindopril (II) having (S)-configuration in all the five chiral centres of the molecule, conforming to pharmacoepeial specifications, and e) it is simple and cost-effective.

The invention claimed is:

1. A process for the synthesis of perindopril of formula (II) and/or pharmaceutically acceptable salts thereof,

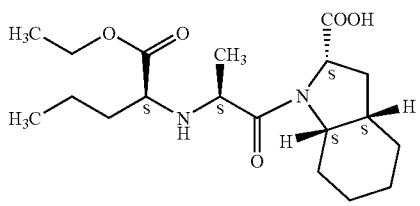

comprising reaction of a compound of formula (I),

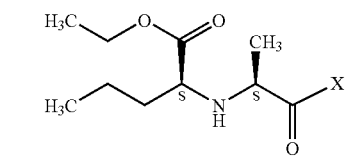

wherein X is chlorine or bromine
with a compound of formula (VII)

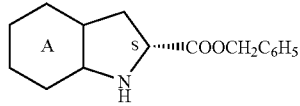

wherein A signifies that the six-membered ring of the bicyclic system is either saturated or unsaturated to give a compound of formula (VIII),

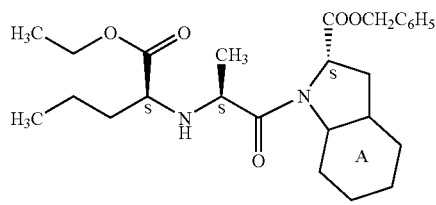

wherein A is as defined above,
followed by catalytic hydrogenation of the compound of formula (VIII) thus obtained to give perindopril of formula (II).

2. A process for the synthesis of perindopril of formula (II) and/or pharmaceutically acceptable salts thereof, as claimed in claim 1

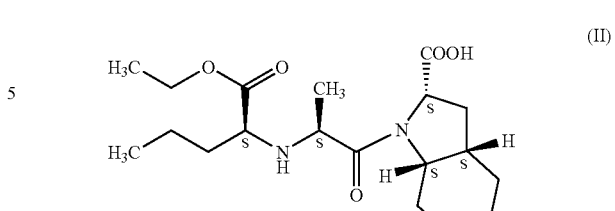

comprising reaction of a compound of formula (I),

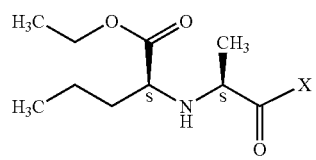

wherein X is chlorine or bromine
with a benzyl ester of (2S, 3aS, 7aS)-2-carboxyperhydroindole of formula (VII-A)

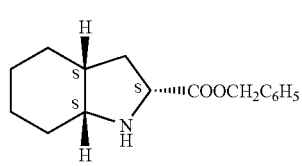

in an organic solvent between –20° C. to +30° C. and in the presence of a base to give a compound of formula (VIII),

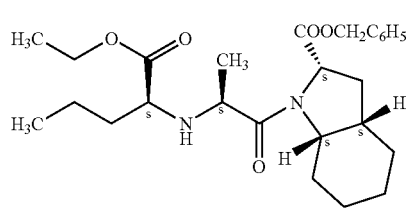

and catalytic hydrogenation of the compound of formula (VIII) to produce perindopril of formula (II).

3. A process for the synthesis of perindopril of formula (II) and/or pharmaceutically acceptable salts thereof, as claimed in claim 1

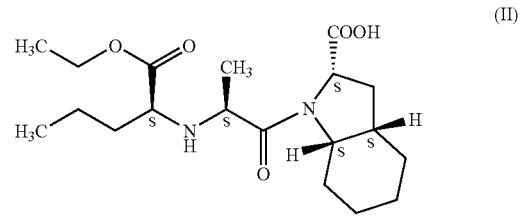

comprising reaction of a compound of formula (I),

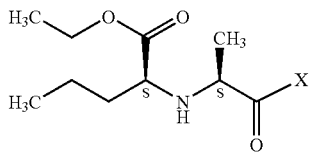

wherein X is chlorine or bromine
with a benzyl ester of indoline-2-(S)-carboxylic acid,

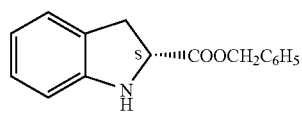

in an organic solvent between −20° C. to +30° C. and in the presence of a base to give a compound of formula (VIII),

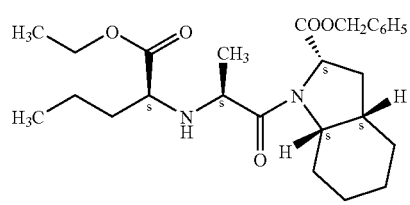

and catalytic hydrogenation of the compound of formula (VIII) to produce perindopril of formula (II).

4. The process according to claim 1, wherein the reaction of the compound of formula (I) with the compound of formula (VII) is carried out in an organic solvent selected from dichloromethane, dichloroethane, benzene, toluene, hexane, heptane, cyclopentane and cyclohexane.

5. The process according to claim 1, wherein the temperature is between −10° C. to −15° C.

6. The process according to claim 1, wherein the molar proportions of compound of formula (VII) is between 0.85 to 0.90 moles per mol of compound of formula (I).

7. The process according to claim 1, wherein the reaction of the compound of formula (I) with the compound of formula (VII) is carried out in the presence of a base selected from diethylamine, triethylamine, pyridine, 2,3-diaminopyridine, 2,4-diaminopyridine, dicyclohexylamine, and N-methyl morpholine.

8. The process according to claim 1, wherein the molar proportions of the base is between 1.0 to 5.0 moles per mole of compound (VII), preferably in molar proportions of 1 to 3.0 moles per mole of compound (VII).

9. The process according to claim 1, wherein the catalytic hydrogenation of compound (VIII) to give compound (II) is carried out in the presence of a Group VIII transition metal catalyst.

10. A The process according to claim 1, wherein the compound (VIII) prior to said catalytic hydrogenation is isolated by evaporation of the organic solvent.

11. A The process according to claim 2, wherein in said step of catalytic hydrogenation the benzyl protective group is cleaved to give said perindopril of formula (II)

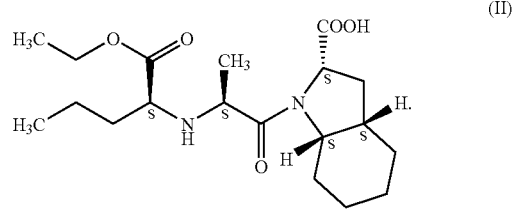

12. The process according to claim 3, wherein said compound (VIII) along with the organic solvent is used for catalytic hydrogenation with concurrent reduction of the aromatic ring and benzylation to give perindopril of formula II.

* * * * *